United States Patent [19]
Knopp et al.

[11] Patent Number: 5,474,548
[45] Date of Patent: Dec. 12, 1995

[54] METHOD OF ESTABLISHING A UNIQUE MACHINE INDEPENDENT REFERENCE FRAME FOR THE EYE

[76] Inventors: Carl F. Knopp, 1301 W. Hillsdale Blvd. No. 205, San Mateo, Calif. 94443; Paul R. Yoder, Jr., 1220 Foxboro Dr., Norwalk, Conn. 06851

[21] Appl. No.: 91,670

[22] Filed: Jul. 14, 1993

[51] Int. Cl.⁶ .................................................. A61B 3/02
[52] U.S. Cl. .............................. 606/4; 606/10; 351/237; 351/246; 128/745
[58] Field of Search .................................. 351/221, 237, 351/239, 246, 243; 606/4, 5, 6, 10, 11, 12; 128/745, 746

[56] References Cited

U.S. PATENT DOCUMENTS

| | | | |
|---|---|---|---|
| 3,861,790 | 1/1975 | Tamura | 351/237 |
| 3,883,234 | 5/1975 | Lynn et al. | 351/243 |
| 4,059,348 | 11/1977 | Jernigan | 351/237 |
| 4,274,715 | 6/1981 | Reiner | 351/243 |
| 4,848,340 | 7/1989 | Bille et al. | 606/4 |

*Primary Examiner*—Stephen C. Pellegrino
*Assistant Examiner*—Sonya Harris-Ogugua
*Attorney, Agent, or Firm*—Thomas M. Freiburger

[57] ABSTRACT

The invention relates to a method and apparatus for uniquely and unambiguously aligning a patient's visual line of sight (LOS) to the optical axis of an ophthalmic instrument such as may be used for laser surgery or diagnostics. By the method of the invention, two alignment targets are imaged at different distances along the optical axis of the ophthalmic instrument. Viewing along the optical axis, a patient moves his or her eye until the two imaged targets are in alignment. When the two imaged targets are viewed in alignment by the patient, the patient's LOS is precisely aligned with the optical axis of the apparatus. By relying on the patient's ability to self-align, this technique ensures that measurements are taken within a reproducible reference frame that is unique to each patient but independent of the type of machine used. The invention is applicable to many instruments and procedures which require precise tracking and positioning of the eye, especially ocular laser surgery devices and various diagnostic instruments employed in tissue imaging or surface topography measurements.

17 Claims, 5 Drawing Sheets

METHOD OF ESTABLISHING A UNIQUE MACHINE INDEPENDENT REFERENCE FRAME FOR THE EYE

BACKGROUND OF THE INVENTION

The invention relates to a method for uniquely aligning a patient's visual line of sight (LOS) to the optical axis of an ophthalmic apparatus that is used for laser surgery or diagnostic measurements. In particular, the invention is useful for surgical laser procedures on the anterior segment of the eye, including but not limited to corneal refractive surgery, and especially wherein such procedures follow a prescription based on prior corneal topographic measurements, thus requiring unique cross-correlation of the patient's LOS between different machines. Other important uses of the invention include, for example, applications involving laser interventions on the retina, especially where correlation with images generated independently by, e.g., a fundus camera, are of advantage.

Ophthalmic surgery using laser beams to modify, for example, the corneal surface or to treat conditions such as glaucoma (by penetrating structures such as the iris or sclera) is a relatively recent development, but has met with substantial success. The precision of a laser intervention typically far exceeds that of mechanical interventions, such as an intervention with a scalpel.

Exploiting the precision of a laser intervention to its fullest requires at least equal precision in locating and tracking critical structures of the eye. In an eye-tracking application involving a sighted eye, there are three functions typically provided to reduce errors in positioning the eye. First, the error in axial location of the eye is measured with respect to a reference location on the apparatus, and the apparatus is accordingly adjusted to reduce this error to a minimum. Second, decentration of the eye with respect to the optical axis of the apparatus is determined, and the apparatus is adjusted to reduce this error to a minimum. Third, the error in angular orientation of the eye's line of sight with respect to a reference direction associated with the apparatus is determined, and the individual is instructed to reduce this error to a minimum by visually fixating on a target.

As an example, many new corneal refractive surgical techniques require the line of sight of the patient's eye to be precisely aligned with the optical axis of the surgical laser instrument. In general, corneal refractive surgery in ophthalmology, including treatment of myopia, hyperopia, and astigmatism, requires, for best results, precise mapping of the topography of the corneal surface so as to establish reference curvatures and/or elevations against which subsequent surface-modifying treatments can be selected and measured. However, to be useful, it is very important to center such topographic measurements upon an axis of the eye that is related to the eye's actual functions and yet can be registered experimentally to the machine axis in an unambiguous manner. The usual method of determining the topography of the cornea is to have the patient look at a small source of light (i.e., a fixation point) while simultaneously placing the patient's head into a "correct" position. This "correct" position is frequently determined by an operator observing the location of reflected light from two projected beams. These two alignment beams can either overlap at a predetermined point along the optical axis of the laser surgical apparatus (i.e. so-called parallax ranging, as used in the Computed Anatomy videokeratography machine and described in U.S. Pat. No. 4,863,260), or the beams may include cross hairs that are projected onto the limbus at the equatorial plane (as used in the EyeSys topography machine).

In conjunction with the fixation point, these alignment beams, in theory, uniquely define the optical axis of the ophthalmic tracking and surgical system and also position the eye the correct distance from the optics of the instrument. However, as will be discussed further below, neither of the above-mentioned approaches using alignment beams is satisfactory for ensuring that measurements have been taken within a reproducible reference frame, i.e., a reference frame that can be relied upon to treat the patient on his or her line of sight (LOS).

The importance of using the LOS as one axis of the reference frame lies in two facts. First, critical vision is centered on the LOS of the eye, irrespective of the direction in which the (mechanical) axis of symmetry of the eye is pointed. Second, the LOS is the only metric of the eye which can be defined without ambiguity (See D. Duke-Elder and D. Abrams, "Ophthalmic Optics and Refraction", Vol. V, In *System of Ophthalmology*, editor D. Duke-Elder, C. V. Mosby Co., St. Louis, 1970, pp. 134–138). By definition, the LOS (which is sometimes referred to as the "principal line of vision") is the chief ray of the bundle of rays passing through the pupil and reaching the fovea, thus connecting the fovea with the fixation point through the center of the entrance pupil. Thus, the line of sight is defined by the patient, which means by the employment of the patient's complete vision system, not by external measurements of the eye, e.g., corneal apex, iris, sclera, retina, limbus, etc., as would be required for determining the axis of symmetry (or the so-called optical axis of the eye).

In particular, it is acknowledged that for best optical performance, it is the intersection of the LOS with the cornea that marks the desired center for the optical zone of refractive surgical procedures, i.e., resulting in the largest zone of glare-free vision.

It should also be noted that the emphasis made herein on clarifying what is meant by the LOS is due to the preponderance in the literature of references to the visual axis, a term which has no clinical significance. In reality the visual axis, which is defined as the hypothetical line connecting the fixation point with the fovea and passing through the nodal points, cannot be experimentally located with any accuracy since the eye is not a centered optical system (the fovea is not located on the optical axis). In fact, it is by definition the LOS which constitutes the most accurate representation of the visual axis in the sense of being amenable to measurement.

Several techniques for aligning the patient's line of sight involve directing the patient to focus on a single fixation point. However, definition of any line requires two conditions. When the patient views a single fixation point, the alignment of the patient to the optical axis of the instrument is dependent upon the ability of the operator to judge, in the parallax ranging method, the overlapping of two beams at the corneal apex or, in the cross hair method, the alignment of two cross hairs upon the limbus. In either case, there is no patient interaction with the machine, other than following directions as to which direction to look or move.

The efficacy of both of the techniques mentioned above is thus seriously compromised by the fact that their alignment is a combination of two separate alignments: translational/angular displacement with respect to the optical axis in a plane perpendicular to the optical axis, and alignment of the eye in distance (focussing) along the instruments optical axis. These two alignments are inextricably intertwined, making a simple focussing action very difficult, if not impossible, to achieve without repeated realignment in the plane perpendicular to the optical axis.

For example, Bille et al., in U.S. Pat. No. 4,848,340, teaches a method of locating the (erroneously labeled) visual axis by directing visible light towards the patient's eye on which he or she can fixate. According to Bille, alignment to the optical axis is considered achieved by this fixation. The fixation aspect of this patent does not, however, specify the apparent distance to the visual target. Furthermore, with a single collimated fixation beam entering the eye (i.e. the target appearing to be at infinity), the observer would have no clue as to errors in transverse alignment, the extent of which corresponds at least to the finite size of the fovea. As such, the methods described in said U.S. Pat. No. 4,848,340 cannot ensure coaxial, much less collinear, alignment of the line of sight to the optical axis of the apparatus because looking at a single point of light (even if at infinity) does not result in a unique (i.e. translation invariant) solution for the LOS.

In view of the above, it is an object of the present invention to provide a method for uniquely aligning the LOS of a patient's eye with the optical axis of an ophthalmological laser surgery or diagnostic instrument, thus providing a means for explicitly ensuring collinearity of the eye's and the machine's chief rays.

SUMMARY OF THE INVENTION

By the method of this invention, alignment of the eye's LOS with the optical axis of an instrument is achieved by providing two alignment targets imaged at different distances along the optical axis of the instrument. A patient looking into the aperture of a projection lens of the instrument can see the imaged targets. Assuming the targets are properly aligned with the optical axis of the instrument, once the patient's LOS is aligned with the optical axis of the instrument, the imaged targets will be aligned with each other as viewed by the patient. However, if the patient's LOS is decentered from the optical axis even by a small amount, the imaged targets will be viewed as offset from each other. This condition is commonly referred to as "parallax".

In the method that is the subject of the present invention, the patient himself provides the alignment. Viewing through the eye that will be the subject of the laser intervention, the patient looks along the optical axis of the apparatus at the two points of reference located along the instrument's optical axis. The patient moves the head back and forth until the two points of reference, as seen through the patient's eye, are in perfect alignment. When the patient views these points of reference in alignment, the patient's line of sight is aligned with the optical axis of the instrument.

Establishment of the patient into the proper position with respect to the treatment instrument is thus guaranteed, to the extent that the patient is able to self-align. Note that in all cases of sighted patients, the patient, as opposed to the operator of the instrument, is relied upon to do the aligning.

In addition to establishing an unambiguous reference frame, this method has the added advantage of decoupling the focussing function (which is accomplished by other means), from the lateral or angular alignment of the patient's eye, and it is therefore both unique and repeatable. Consequently, the invention fulfills an important function whenever cross-registration of data between different ophthalmic apparatus is required, such as between laser surgery and diagnostic instruments, including but not limited to corneal topography devices, confocal microscopes, or (in applications involving the retina) fundus cameras.

DESCRIPTION OF THE DRAWINGS

FIGS. 2A to 3B illustrate optical principles on which the invention is based.

FIG. 2A illustrates a single-target fixation method for aligning an eye with the optical axis of an instrument.

FIG. 3B shows an apparatus for projecting a target onto an optical axis at a finite distance.

DESCRIPTION OF THE PREFERRED EMBODIMENTS

Figure 1:
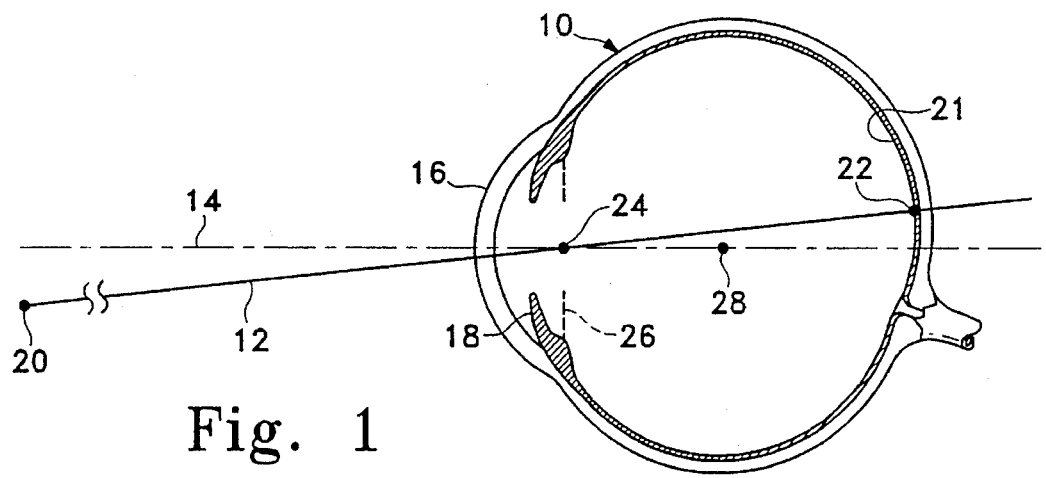
FIG. 1 is a cross-sectional view of a patient's eye.

FIG. 1 is a cross-sectional view of a patient's eye 10 with two of the key axes, the LOS 12 and axis of symmetry 14, marked as commonly defined. At the front of the eye is the cornea 16 which admits light through the iris 18 where it is focused by the combined imaging properties of the cornea and the crystalline lens (not shown). In a normal eye, the image of a distant target 20 is formed at the retina, which lines the interior of the rear surface 21 of the eyeball. The portion of the retina with highest resolution is the fovea 22, which is located slightly temporally from the axis of symmetry of the eye's optical surfaces (also known as the geometric axis). The point "EP" 24 in FIG. 1 represents the center of the entrance pupil 26 of the eye's optical system. The entrance pupil 26 is the image of the eye's iris 18 as seen through the cornea. The center of rotation 28, located along the eye's axis of symmetry, is the point about which the eye rotates in its socket. The line of sight 12 of the eye emanating from the target 20 (fixation point) passes through EP 24 and the fovea 22. This line of sight (LOS) is typically inclined at an angle (kappa) of about 6 degrees to the axis of symmetry 14 of the eye for an eye with a centered iris.

Often confused with the LOS is the so-called visual axis, which in reality cannot be experimentally determined. It is defined as the line connecting the fixation point with the fovea and passing through the lens' nodal points. It would constitute an optical axis if the eye were a centered optical system. However, since the eye's optics are acentric, the true visual axis is meaningless for all practical purposes, and most measurements involving a fixation source are concerned with the LOS.

Figure 2A:
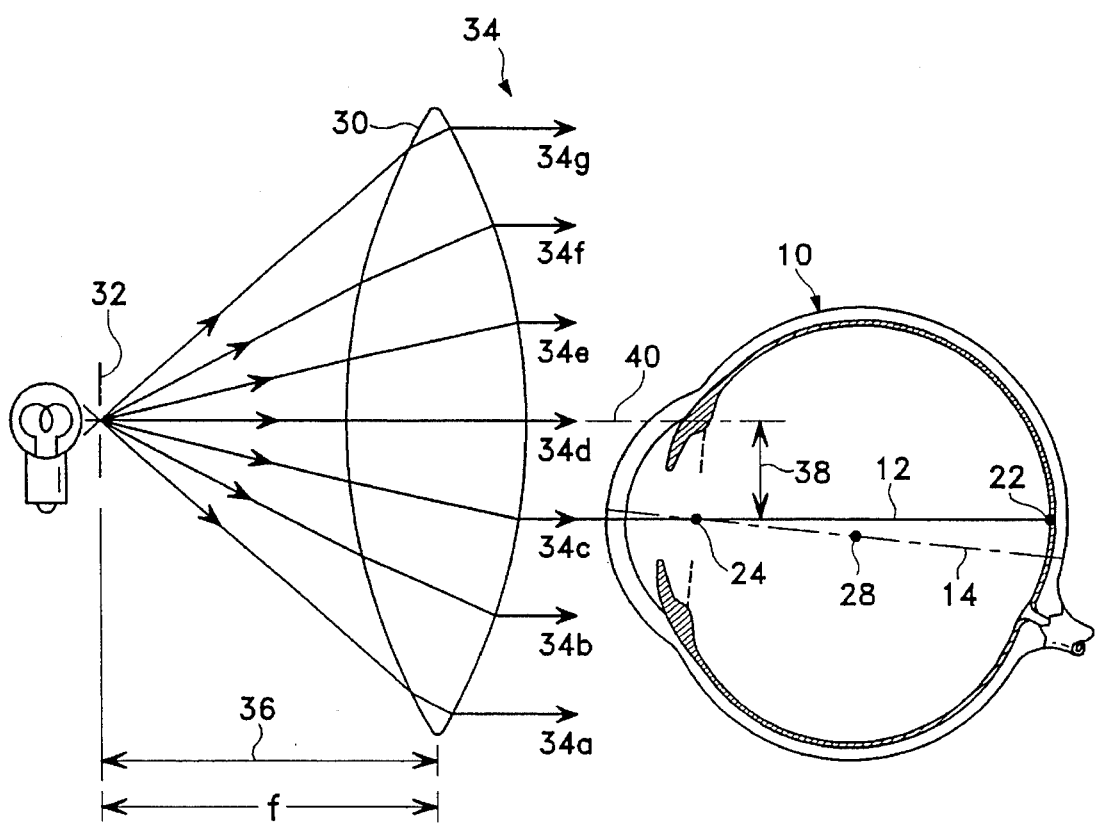
Figure 2B:
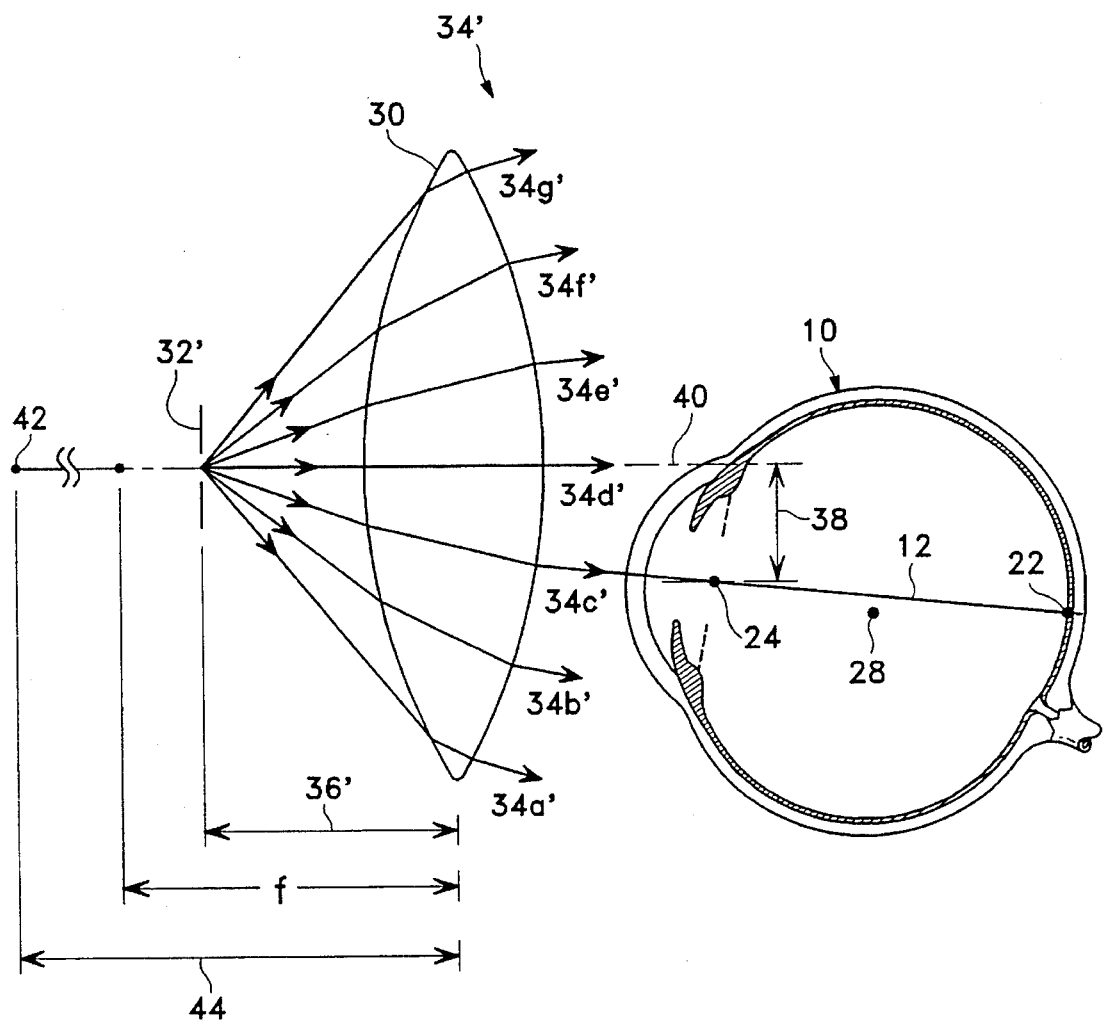
FIG. 2B illustrates another single-target fixation method for aligning an eye with the optical axis of an instrument.

FIGS. 2A and 2B illustrate single-target fixation methods for aligning an eye with the optical axis of an instrument. In FIG. 2A, an eye 10 is shown looking into the aperture of a projection lens 30 (the lens aperture is shown as the entire lens) that reimages an illuminated target 32 at an infinite distance, i.e., the beam 34 is collimated.

The illuminated target 32 in FIG. 2A is shown reimaged at an infinite distance, which is achieved by having the target object distance 36 equal to the lens focal length f, i.e. the target is at the lens focal point. To first-order approximation, the relationship between object and image distances for a lens of focal length f follows the familiar Gaussian equation (1/l')=(1/f)+(1/l) where l and l' are respectively the object and image distances measured from the lens center. Because the illuminated target appears at an infinite distance as viewed by the eye, individual light rays 34a to 34g are parallel to each other.

FIG. 2A shows the eye 10 fixated on the target 32 along ray 34c, which appears to come from the target as imaged by the projection lens 30. The eye is here decentered a distance 38 from the optical axis 40 of the instrument. This decentration of the eye with respect to the optical axis of the instrument does not affect fixation to an infinitely distant image since all rays projected by the lens are parallel. As such, in an instrument that relies on fixation to a single target imaged at infinity, an eye can be fixated on the target but still be off-center of the optical axis of the instrument.

FIG. 2B shows the same situation as in FIG. 2A except that the target 32' is located somewhat closer to the projection lens 30 so that the image 42 appears at a large but finite distance 44 behind the lens. As was the case in FIG. 2A, the eye 10 in FIG. 2B is fixated on the target 32' along a ray 34c, which is off-center. However, the rays 34a' to 34g' projected by the lens shown in FIG. 2B are seen to diverge as if they originated at the apparent image of the target, which is located on the lens axis at a finite distance 44 from the lens. If the decentration 38 of the eye in FIG. 2B changes, the eye must rotate somewhat about its center of rotation 28 in order to fixate on that image. The eye in FIG. 2B is shown rotated by some angle so as to align its LOS to the direction of propagation of ray 34c'. Thus, a decentered eye fixated on a finite-distance target is not merely off-center but is also angularly offset from the optical axis of the instrument.

Figure 3A:
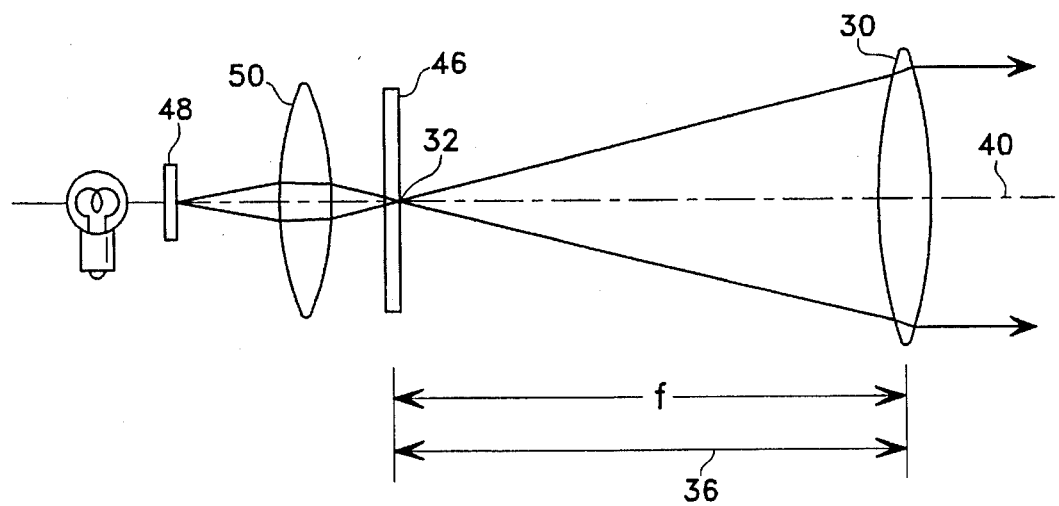
FIG. 3A shows an apparatus for projecting a target onto an optical axis at an infinite distance.

FIG. 3A shows a simple embodiment of a projection lens 30 used to create an optical image at infinite distance, as was schematically shown in FIG. 2A. The target 32 typically is a back-illuminated pattern on a transparent glass reticle 46. This target is located at a distance 36 on the lens' optical axis 40 at the lens' focal point, i.e. where l=f. A diffusing plate 48 and condensing lens 50 are used to ensure full illumination of the target pattern 32 throughout the projection lens aperture. Rays projected by the projection lens 30 are more or less parallel depending upon the degree of imaging perfection achieved in the optical system. Assuming a well-corrected lens with small aberrations, the image as observed through the lens aperture will appear to be at infinity.

Figure 3B:
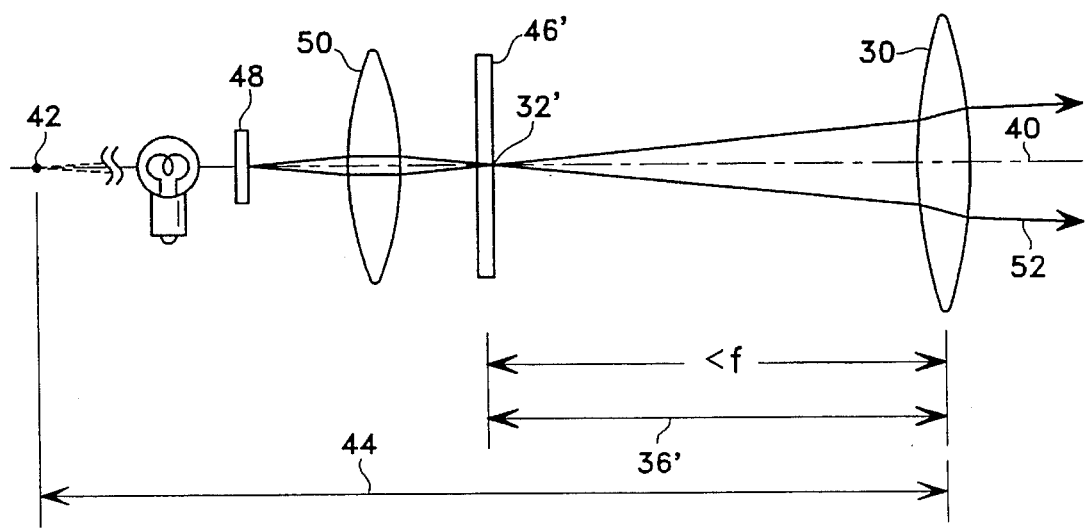

FIG. 3B shows a somewhat different optical system in which a target 32' is projected to appear at a point 42 located a finite distance 44 behind the lens 30, as was shown schematically in FIG. 2B. The diffusing plate 48 and condensing lens 50 are again used to ensure that full illumination of the target pattern is achieved throughout the projection lens aperture. In the system of FIG. 3B, the target 32' is located at an object distance 36', which is inside the focal point in accordance with the aforementioned Gaussian equation, so that l<f. The path of a typical ray of light 52 from the center of the target 32' is shown. If the eye is aligned to this ray, the target is observed as if it were located at the point 42, i.e. at a finite distance. This ray would then be similar to ray 34c' of FIG. 2B, and fixation of the eye could be established as appropriate for the given degree of decentration from the optical axis 40.

Figure 4:
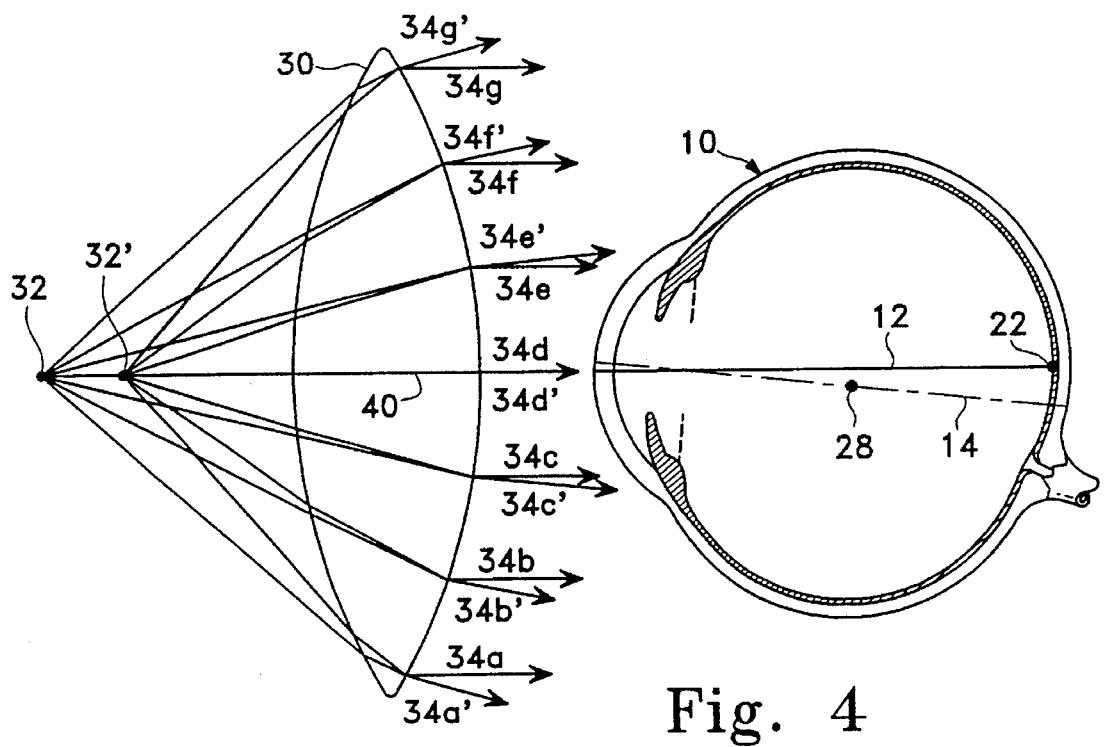
FIG. 4 illustrates the dual-target fixation method of the invention.

FIG. 4 illustrates the fixation method of the present invention, whereby the single-target fixation methods shown in FIGS. 2A and 2B are both used simultaneously in a dual-target fixation system. With two fixation targets 32 and 32' at different distances, the eye 10 will see angular disparity (parallax) between the target images (i.e., they will not appear to be superimposed) if the eye is decentered. The rays 34a to 34g of the infinite-distance target 32 are parallel to one another, while the rays 34a' to 34g' of the finite distance target 32' diverge. The only rays of the targets that coincide are rays 34d and 34d', which are coaxially aligned along the optical axis 40 of the instrument (the details of the ophthalmic instrument in which this apparatus is incorporated are not shown). Thus, the eye can only be simultaneously fixated on both targets if the eye's line of sight 12 is centered on the optical axis, ie. along the ray 34d (which is the same as 34d'). Only when the line-of-sight of the eye lies on the optical axis 40 of the apparatus can both images be fixated.

Figure 5:
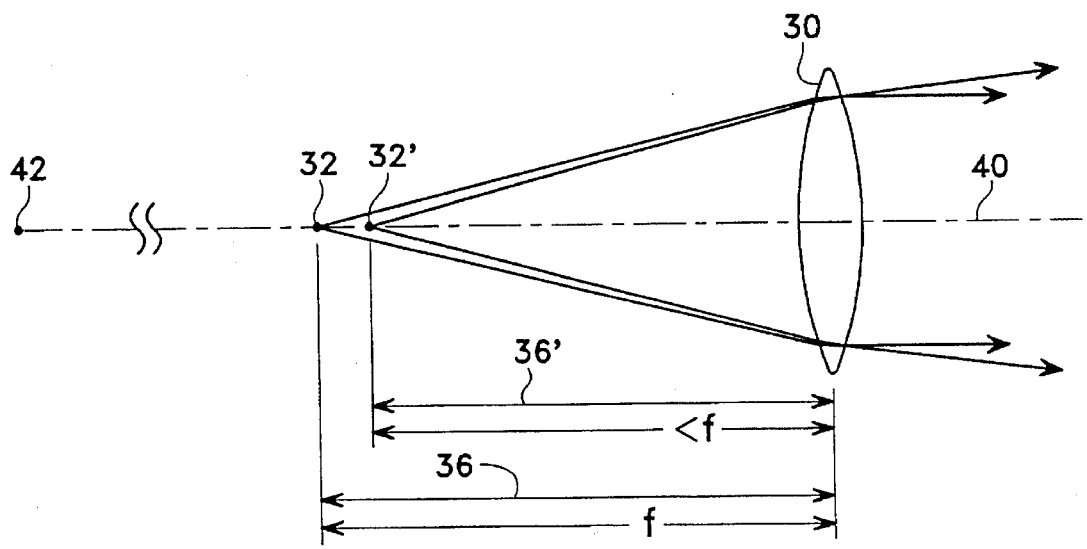
FIG. 5 is a simplified view of an apparatus with which two reticle patterns can be projected simultaneously by the same projection lens to provide fixation targets at a large distance (such as infinity) and a shorter (finite) distance.

FIG. 5 shows schematically an apparatus with which two reticle patterns could be projected simultaneously by the same projection lens to provide fixation targets 32 and 32' at a large distance 36 (such as infinity) and a shorter (finite) distance 36'. It is preferable that both fixation targets are at relatively large distances so that only slight focus accommodation of the eye is required to compensate for these different distances. By instructing the patient to move his or her eye transversely with respect to the apparatus axis until angular displacement (parallax) between the images is minimized, alignment of the eye to the optical axis 40 of the apparatus is facilitated. In surgical procedures where the sighted eye must be accurately aligned to an optical apparatus in order for the procedure to be successful, providing two fixation targets at different apparent distances will simplify such alignment while enhancing its accuracy.

Figure 6:
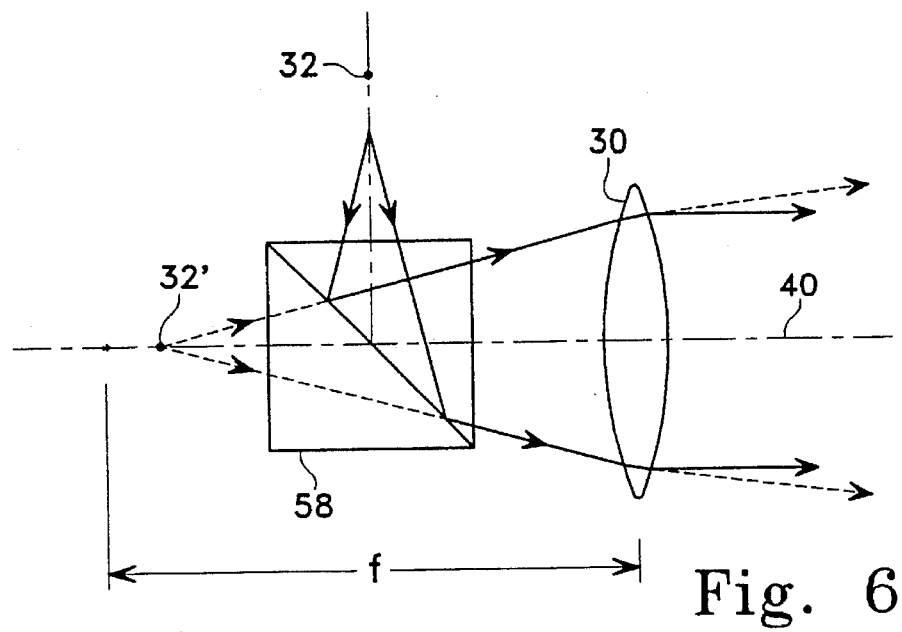
FIG. 6 shows another embodiment of an apparatus for combining two reticle patterns to project them simultaneously at different axial distances.

FIG. 6 shows another embodiment of an apparatus for combining two reticle patterns 32 and 32' to project them simultaneously at different axial distances. A beamsplitter plate or cube 58 is inserted between the patterns and projection lens 30 so each pattern can be illuminated independently. In both embodiments (FIGS. 5 or 6), the patterns can be opaque lines seen against a light background, bright lines seen against a dark background, or a combination of these forms.

Figure 7A:
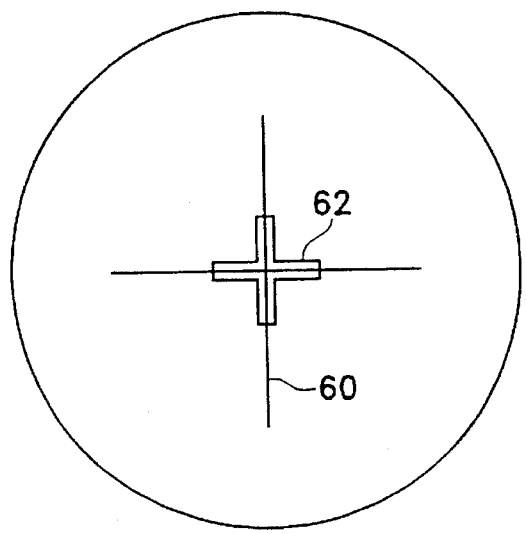
FIG. 7A shows an example of a typical dual pattern as viewed by the patient when the patterns are in alignment

FIG. 7A shows an example of a typical dual pattern as viewed by the patient when the patterns are in alignment, ie. when the patient's eye is aligned with the optical axis of the apparatus. The dual pattern set in this particular embodiment comprises an opaque fine-line cross 60 seen against a broader bright cross 62. The use of color in one or both patterns may be helpful. It is not necessary that the targets appear as crosses; patterns such as circles, dots, squares, etc. also can suffice.

Figure 7B:
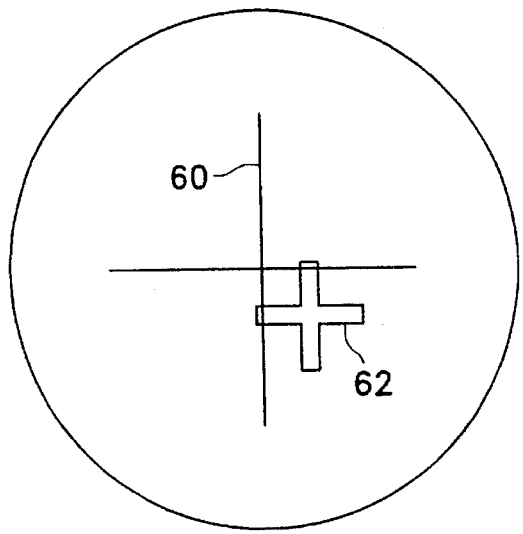
FIG. 7B shows the dual pattern of FIG. 7A when the patterns are offset.

FIG. 7B shows the same dual pattern set as shown in FIG. 7A, except the patterns are offset, indicating that the eye is decentered with respect the optical axis of the associated optical instrument.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for aligning the line of sight of a patient's eye to an optical axis of an ophthalmic instrument, said instrument having an aperture through which the patient may look along the optical axis, comprising the steps of:

imaging a first reference target on said ophthalmic optical axis of the instrument with said optical device, imaging a second reference target on the optical axis of the instrument with an optical device, said second reference target being imaged, with respect to the patient's eye, at an optical distance farther along the optical axis than the first reference target, and effecting movement of the patient's eye laterally to a position where the images of the first and second reference targets appear in alignment as viewed by the patient's eye.

whereby the patient's line of sight and the optical axis of the instrument are aligned.

2. The method of claim 1, wherein the step of moving the patient's eye is performed by the patient.

3. The method of claim 2, wherein the second reference target is imaged at infinity behind the aperture, and the first reference target is imaged at a finite distance from the aperture.

4. The method of claim 2, including the further step of illuminating at least one of the images of the reference targets prior to the step of moving the patient's eye.

5. The method of claim 4, wherein the images of both reference targets are illuminated.

6. The method of claim 1, wherein the ophthalmic instrument is an ophthalmic laser surgery workstation, and further including the step of conducting a laser surgical intervention on the eye with the line of sight of the patient's eye aligned with the optical axis of the instrument.

7. A system for ophthalmological applications, comprising:

optics means for directing and focusing light onto a patient's eye, said optics means defining an optical axis and including an aperture through which a patient can look along the optical axis, and said optics means including first means for producing an image of a first reference target along the optical axis of the system, viewable by the patient through the aperture, second means for producing an image of a second reference target along the optical axis of the system, viewable by the patient through the aperture, and including means for producing the image of the second reference target to appear more distant from the patient's eye than the image of the first reference target, whereby the images of said first and second reference targets define a line which is axially aligned with the optical axis of the system, and alignment of the patient's line of sight to the optical axis of the system is indicated by apparent alignment of the two reference targets as seen by the patient's eye.

8. The system of claim 7, wherein the second means includes means for projecting the image of the second reference target on the optical axis at an infinite optical distance from the aperture.

9. The system of claim 7, wherein the first and second means include means for producing at least one of the images of the first and second reference targets as a transparent image.

10. The system of claim 7, wherein the first and second means include means for producing at least one of the images of the first and second reference targets as an opaque image.

11. The system of claim 7, wherein the first and second means include means for producing the image of the first reference target in a different color from the image of the second reference target.

12. The system of claim 7, wherein the optics means includes means for projecting a laser beam, the laser beam having sufficient power to conduct surgical intervention in the patient's eye.

13. The system of claim 7, wherein the first and second means include means for producing the images of the first and second reference targets as interlocking shapes, whereby a patient may easily locate a position of line of sight alignment of the patient's eye with respect the optical axis.

14. The system of claim 13, wherein the projected image of the first reference target defines a hollow cross, and the projected image of the second reference target defines a solid cross, said projected images of first and second reference targets being sized so that, when viewed by a patient's eye the line of sight of which is aligned with the optical axis, the solid cross of the second reference target precisely fills the hollow cross of the first reference target.

15. The system of claim 13, wherein the projected image of the first reference target defines a dark fine-line cross, and the projected image of the second reference target defines a bright cross, said bright cross being wider than the fine-line cross, whereby when said first and second projected images of the reference targets are aligned as viewed by the patient, the dark fine-line cross is centered upon the wider bright cross.

16. The system of claim 15, wherein the bright cross is illuminated.

17. The system of claim 13, wherein the projected image of the first reference target defines a hollow distinctive shape, and the projected image of the second reference target defines a solid distinctive shape, the projected images of said first and second reference targets being sized so that, when viewed by a patient's eye the line of sight of which is aligned with the optical axis, the solid distinctive shape of the second reference target's image appears superimposed to substantially fill the hollow distinctive shape of the first reference target's image.

* * * * *